| United States Patent [19] | [11] Patent Number: 4,761,478 |
| Pattison | [45] Date of Patent: Aug. 2, 1988 |

[54] 3-DEAZAGUANINE SULFONIC ACID SALTS

[75] Inventor: Ian C. Pattison, Ann Arbor, Mich.

[73] Assignee: Warner-Lambert Company, Morris Plains, N.J.

[21] Appl. No.: 821,176

[22] Filed: Jan. 21, 1986

Related U.S. Application Data

[63] Continuation-in-part of Ser. No. 409,389, Aug. 19, 1982, abandoned.

[51] Int. Cl.[4] ............................................ C07D 471/04
[52] U.S. Cl. ................................................... 546/118
[58] Field of Search ........................ 546/118; 514/303

[56] References Cited

U.S. PATENT DOCUMENTS

| 4,056,674 | 11/1977 | Robins et al. | 548/343 |
| 4,147,700 | 4/1979 | Hirai et al. | 548/265 |
| 4,197,297 | 4/1980 | Weinstock | 514/213 |
| 4,376,858 | 3/1983 | Colbry | 544/291 |

*Primary Examiner*—Jane T. Fan
*Attorney, Agent, or Firm*—Jerry F. Janssen

[57] ABSTRACT

Sulfonic acid salts, and particularly the methanesulfonic acid salt of 6-amino-1,5-dihydro-4H-imidazo-[4,5-c]pyridin-4-one (3-deazaguanine) possess unexpected solubility in water and are thus useful in preparing pharmaceutical compositions having the requisite stability, clarity, and potency for parenteral administration.

1 Claim, No Drawings

3-DEAZAGUANINE SULFONIC ACID SALTS

CROSS-REFERENCE TO RELATED APPLICATIONS

This application is a continuation-in-part of application Ser. No. 409,389 filed Aug. 19, 1982, now abandoned.

BACKGROUND OF THE INVENTION

The compound 6-amino-1,5-dihydro-4H-imidazo[4,5-c]pyridin-4-one (3-deazaguanine) is descrobed and claimed in U.S. Pat. No. 3,896,135. The patent describes the compound as possessing antiviral and antibacterial activity. More recent reports have described the compound as also possessing antitumor activity [J. Am. Chem. Soc., 98: 1492 (1976)]. Drug administration by the parenteral route, especially the intravenous route, for this last indication is preferred.

U.S. Pat. No. 3,896,135 also discloses that 3-deazaguanine forms salts with bases such as sodium hydroxide and with acids such as hydrochloric and sulfuric. Unfortunately, investigation has shown that these salts are not suitable for preparing parenteral dosage forms. Thus, an aqueous solution of the sodium salt form possesses a pH at which 3-deazaguanine is chemically unstable. The hydrochloric and sulfate forms are poorly soluble so that administration of aqueous parenteral solutions of these salts is impractical. In fact, it has been found that the sulfate salt is only about one-half as soluble as the corresponding free base. This observation is quite surprising and is the reverse of characteristic increase of solub8ility of acid addition salts of basic compounds.

SUMMARY OF THE INVENTION

The present invention provides certain substituted sulfonic acid salts of 3-deazaguanine. These salts are unexpectedly highly water soluble and may be utilized to produce convenient pharmaceutical dosage forms. In particular, the salts may be utilized to produce dosage forms which are suitable for parenteral administration. The parenteral dosage forms may be in the form of solutions, suspensions, or dry solid forms which are reconstituted with a suitable liquid prior to administration.

In its broadest chemical compound aspect, the present invention provides compounds of structural formula I.

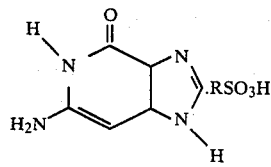

wherein R is phenyl or $R_1CH_2$ wherein $R_1$ is hydrogen or alkyl of from one to six carbon atoms which may be substituted with one or more hydroxyl groups.

In a first sub-generic chemical compound aspect, the present invention provides compounds of structural formula I wherein $R_1$ is hydrogen or unsubstituted alkyl of from one to six carbon atoms.

In a second sub-generic chemical compound aspect, the present invention provides compounds of structural formula I wherein $R_1$ is alkyl of from one to six carbon atoms which is substituted with one or more hydroxyl groups.

In its pharmaceutical composition aspect, the present invention provides stable, pharmaceutical composition suitable for parenteral administration comprising a solution containing at least 15 mg/ml of a compound of structural formula I above, wherein R and $R_1$ are as previously defined, dissolved in a pharmaceutically acceptable solvent.

DETAILED DESCRIPTION

The free base, 6-amino-1,5-dihydro-4H-imidazo[4,5-c]pyridin-4-one, may be prepared by procedures detailed in U.S. Pat. No. 3,896,135. The teachings of this patent are incorporated herein by reference.

The substituted sulfonic acids utilized to prepare the final compounds of this invention are either commercially available, or are prepared by standard procedures known in the art.

The salts of this invention may be prepared by standard procedures. This, approximately equivalet amounts of 3-deazaguanine free base and the desired salt-forming sulfonic acid are combined in that volume of solvent (such as water) necessary to obtain complete solution. The solvent may be removed after salt formation is complete by, for example, lyophilization and the residue purified if desired by standard techniques such as recrystallization.

Alternatively, approximately equivalent amounts of 3-deazaguanine free base and the desired sulfonic acid may be combined in a minimum volume of solvent to produce a suspension. The suspension may be moderately heated to produce complete solution. The salt produced by this process is isoltaed and purified, if necessary, as described above. Solvents other than water may be utilized for the preparation of the salts. Examples of such solvents are alcohols such as methanol, ethanol, propanol and the like; ketones such as propanone, butanone, and the like; N,N-dimethylformamide; dimethylsulfoxide; as well as mixtures thereof.

For preparing individual sterile dosage forms, the appropriate volume of solution containing a compound of this invention may be sterilized by filtration through membrane filters into previously sterilized containers such as vials. The vials containing the parenteral solutions may be sealed or capped or, alternatively, the solvent may be removed by lyophilization and the containers then closed by sealing or capping.

Dosage forms containing the compound in dry, stable form may be reconstituted with the appropriate solvent or suspending medium prior to use. Suitable solvents and suspending media are exemplified by pharmaceutically acceptable solvents or mixtures thereof such as distilled water, sterile water, sterile isotonic media such as glucose solution, ethanol, ethylene glycol, propylene glycol and the like; as well as mixtures thereof. The reconstituted dosage form may be in the form of a solution useful for intravenous administration, or in the form of a suspension useful for intramuscular administration.

Similar individual sterile dosage forms may also be prepared by sterile filling of appropriate containers with a compound in accordance with this invention in the dry solid form. Procedures for performing the dry sterile fill operation are familiar to those skilled in the pharmaceutical formulation arts.

Alkyl groups contemplated by this invention designated by the symbol $R_1$ may be both branched and straight chain of from one to six carbon atoms. Examples of such groups are methyl, ethyl, propyl, iso-propyl, butyl, tert-butyl, pentyl, 3-methylpentyl, hexyl and the like. The preferred alkyl groups are composed of from one to about three carbon atoms.

The alkyl groups, in addition, may be substituted with one or more hydroxyl groups. Those skilled in the art will recognize that only one hydroxyl group may be substituted on any particular carbon atom. The preferred hydroxylated alkyl groups contain up to about three carbon atoms and therefore contain no more than three hydroxyl groups, each located on different carbon atoms of the chain. Examples of preferred hydroxylated alkyl groups are $HOCH_2-$, $HOCH_2CH_2-$, $CH_3CH(OH)-$, $HOCH_2CH(OH)CH_2-$, and the like.

The preferred chemical compound of the present invention is that wherein $R_1$ is hydrogen, that is, 3-deazaguanine methanesulfonic acid salt.

Certain of the alkyl groups of this invention may possess an asymmetric carbon atom and therefore be possible of existing in different optical isomeric forms. The pure isomers as well as the mixtures thereof are contemplated by this invention.

The compounds of the invention may exist in unsolvated as well as solvated forms, including hydrated forms. In general, the solvated forms with pharmaceutically acceptable solvents such as water, ethanol, and the like are equivalent to the unsolvated forms for the purposes of this invention.

In order to formulate a drug for liquid form intravenous administration, it is critical that the form of the drug employed be both stable and completely soluble in the liquid vehicle employed. In the case of 3-deazaguanine which is capable of forming both base and acid addition salts, it has been found that the comnon base addition salts such as the sodium salt possess a pH in aqueous solution causing the compound to be unstable. Water solutions of the sodium salt of 3-deazaguanine tend to begin to degrade within a few hours of formulation.

Consequently, to formulate a stable salt form of 3deazaguanine, it is necessary to utilize an acid addition salt. In this case, the solubility of the salts formed with the more commonly employed acids is too low to permit the preparation of solutions suitable form parenteral administration which contain a sufficiently potent dose of the drug.

The common acids employed for the formulation of acid addition salts of pharmaceutical bases are listed in *J. Pharm. Sciences*, 66 (No. 1): 1–19 (1977). Table I shows the solubilities of a number of acid addition salts of 3-deazaguanine. The solubility values presented in Table I were determined as follows: 3-deazaguanine (250 mg) was suspended in a small volume of water and one equivalent weight of the acid was added with stirring. Stirring was continued and small volumes of water were added intermittently until complet solution was obtained.

TABLE I

| Solubilities of 3-Deazaguanine Salts | | | |
| --- | --- | --- | --- |
| Acid | ml Water Needed to Dissolve | Solubility mg/ml | Relative Solubility of Salt to Free Base* |
| Free base | 100–125 | 2.0–2.5 | 1.0 |
| HCl | 65–75 | 3.3–3.8 | 1.9 |
| $H_2SO_4$ | 250–300 | 0.8–1.0 | 0.5 |
| $H_3PO_4$ | 120–130 | 1.9–2.1 | 1.05 |

TABLE I-continued

| Solubilities of 3-Deazaguanine Salts | | | |
| --- | --- | --- | --- |
| Acid | ml Water Needed to Dissolve | Solubility mg/ml | Relative Solubility of Salt to Free Base* |
| Acetic | 85–95 | 2.6–2.9 | 1.45 |
| Citric | 170–180 | 1.4–1.5 | 0.75 |
| Maleic | 150–160 | 1.6–1.7 | 0.85 |
| d-Tartaric | 150–160 | 1.6–1.7 | 0.85 |
| Methanesulfonic | 5 | 50 | 25 |
| Hydroxyethanesulfonic | 5–10 | 25–50 | 25 |
| Ethanesulfonic | 10 | 25 | 12.5 |
| Benzenesulfonic | 25 | 10 | 5.0 |

*These values were obtained by dividing the higher value of the solubility range for the particular salt by the 2.0 mg/ml solubility of the free base.

The data presented in Table I demonstrate the water solubility advantage for the compounds of the present invention. The solubility advantage of the organic sulfonate salts, particularly the preferred methanesulfonate salt of this invention, is surprising in light of the lower solubility of the sulfate salt over the free base.

It is not generally the case with organic nitrogenous bases that the methanesulfonate salt is the preferred salt of choice when increased solubility is required. For example, Table II presents solubility data for acid addition salts of the compound 2,4-diamino-5-methyl-6-[[(3,4,5-trimethoxyphenyl)amino]methyl]quinazoline (trimetrexate) arranged in decreasing order of solubility.

TABLE II

| Solubility of Trimetrexate Acid Addition Salts in Water | |
| --- | --- |
| Acid | Solubility (mg/ml) |
| Glucuronic | 34.35 |
| Galacturonic | 25.1 |
| Gluconic | 19.8 |
| Ethoxyacetic | 19.5 |
| Isethionic | 17.3 |
| N—Morpholinoethane-2-sulfonic | 11.2 |
| Methanesulfonic | 9.83 |
| Citric | 8.28 |
| Benzenesulfonic | 7.17 |
| Glycolic | 4.73 |
| p-Toluenesulfonic | 1.73 |
| d-Tartaric | 1.57 |
| 2-Aminoethanesulfonic | 0.51 |
| 2-Naphthalenesulfonic | 0.15 |

(Data from U.S. Pat. No. 4,376,858)

As the data shown in Table II indicate, the organic sulfonic acid salts are among the least soluble of the salts tested for this compound, the methanesulfonate salt in particular being sixth in order of solubility.

Similarly, as shown by the data presented in Table III, the methanesulfonate salt is one of the least soluble salts prepared the the compound 4'-(9-acridinylamino)methanesulfon-m-anisidide (m-AMSA).

TABLE III

| Relative Solubility of m-AMSA Acid Addition Salts | |
| --- | --- |
| Acid | Solubility Relative to Free Base |
| Galacturonic | 6133 |
| Glucose-6-phosphoric | 3785 |
| Gluconic | 2815 |
| Ascorbic | 1213 |
| β-Glycerophosphoric | 1085 |
| Glucuronic | 923 |
| Lactic | 890 |
| Glyceric | 555 |
| Citric | 438 |

TABLE III-continued
Relative Solubility of m-AMSA Acid Addition Salts

| Acid | Solubility Relative to Free Base |
| --- | --- |
| Acetic | 234 |
| Propionic | 225 |
| Gallic | 225 |
| Isethionic | 213 |
| Malonic | 192 |
| D,L-Malic | 165 |
| Succinic | 154 |
| d-Tartaric | 138 |
| Glutaric | 102 |
| Mucic | 33 |
| Phosphoric | 29 |
| Salicylic | 18 |
| Glycolic | 18 |
| Benzoic | 10 |
| Methanesulfonic | 7.5 |
| Gentisic | 7.5 |
| Sulfuric | 6 |
| Nitric | 3 |
| Sulfamic | 2.8 |
| Hydrochloric | 1.2 |
| Free base | 1 |

(Data from EPO Patent 0035862.)

The following examples are provided to enable one skilled in the art to practice the present invention. These examples are not to be read as limiting the scope of the invention, but are merely illustrative of the invention as it is defined by the appended claims.

EXAMPLE I

Preparation of 3-deazaguanine methanesulfonate salt

To a slurry of 24.5 g of 6-amino-1,5-dihydro-4H-imidazo-[4,5-c]pyridin-4-one (3-deazaguanine) in 250 ml of methyl alcohol was added a solution of 17.0 g of methanesulfonic acid in 50 ml of methyl alcohol. The mixture was stirred at room temperature for about 10 minutes, filtered, and the filter cake washed with methyl alcohol to give, after drying, 35.5 g (88%) of 3-deazaguanine methanesulfonate salt, mp 273°–275° C. This material produced a solution in water at a concentration of 41 mg/ml which remained clear and free of any precipitate for more than three days.

A 1.0 g sample of this salt was recrystallized from 22 ml of 80% aqueous methyl alcohol to give material melting at 281°–283° C.

PHARMACEUTICAL COMPOSITIONS

Example 1

| Ingredient | Quantity |
| --- | --- |
| 3-Deazaguanine methane-sulfonic acid salt | 300 g |
| Lactose | 974 g |
| Corn starch | 39 g |
| Hydroxypropyl cellulose | 30 g |
| Magnesium stearate | 7 g |
| Ethanol-water 50:50 | qs |

The 3-deazaguanine methanesulfonic acid salt, lactose, and hydroxypropyl cellulose are blended and granulated with the 50:50 mixture of ethanol and water. The wet granulation is screened, dried, and rescreened. The resulting dried granulation is blended with magnesium stearate and corn starch, and the mixture is compressed into 450 mg tablets using an 11/32 inch standard concave punch. Yield equals approximately 3000 tablets each containing 100.0 mg of 3-deazaguanine methanesulfonic acid salt.

Example 2

| Ingredient | Quantity |
| --- | --- |
| 3-Deazaguanine methane-sulfonic acid salt | 1000 g |
| Lactose | 1900 g |
| Corn starch | 50 g |
| Hydroxypropyl cellulose | 40 g |
| Magnesium stearate | 10 g |
| Ethanol-water 50:50 | qs |

The 3-deazaguanine methanesulfonic acid salt, lactose, and hydroxypropyl cellulose are blended and granulated with the 50:50 mixture of ethanol and water. The wet granulation is screened, dried, and rescreened. The resulting dried granulation is blended with magnesium stearate and corn starch, and the mixture is compressed into 750 mg tablets using a standard concave punch. Yield equals approximately 4000 tablets each containing 250.0 mg of 3-deazaguanine methanesulfonic acid salt.

Example 3

| Ingredient | Quantity |
| --- | --- |
| 3-Deazaguanine methane-sulfonic acid salt | 500 g |
| Lactose | 1473 g |
| Magnesium stearate | 27 g |

The mixture is blended and filled into hard gelatin capsules, filling each capsule with 400 mg of the powder mixture. Yield equals approximately 5,000 capsules each containing 100.0 mg of 3-deazaguanine methanesulfonic acid salt.

Example 4

| Ingredient | Quantity |
| --- | --- |
| 3-Deazaguanine methane-sulfonic acid salt | 1000 g |
| Lactose | 1950 g |
| Magnesium stearate | 50 g |

The mixture is blended and filled into hard gelatin capsules, filling each capsule with 750 mg of the powder mixture. Yield equals approximately 4,000 capsules each containing 250.0 mg of 3-deazaguanine methanesulfonic acid salt.

Example 5

| Ingredient | Quantity |
| --- | --- |
| 1. Methanesulfonic acid (98% solution) | 18.2 g |
| 2. 3-Deazaguanine free base | 25.0 g |
| 3. Water for injection | qs ad 1000 ml |
| 4. Nitrogen gas (high purity) | qs |

In a suitable container, mix 1 with approximately 725 ml of 3 to yield solution A. Add 2 to solution A with mixing until 2 is dissolved. Add a sufficient amount of 3 to make 1000 ml of solution and mix well. Sterilize the final solution by filtering through appropriate prefilters followed by filtration through a previously sterilized membrane, using 4 for positive pressure. Aseptically fill 10.0 ml of the solution into previously sterilized vials. Stopper loosely with lyophilization closures and lyophilize. Cap the lyophilized vials.

When reconstituted with 10 ml of steril water for injection, the resulting solution will contain 25 mg/ml of 3-deazaguanine methanesulfonic acid salt.

What is claimed is:

1. The compound having the name 6-amino-1,5-dihydro-4H-imidazo-[4,5-c]pyridin-4-one methanesulfonic acid salt, said compound having improved solubility in water.